United States Patent
Reddy et al.

(10) Patent No.: US 6,656,968 B1
(45) Date of Patent: Dec. 2, 2003

(54) (Z)-STYRYL ACETOXYPHENYL SULFIDES AS CYCLOOXYGENASE INHIBITORS

(75) Inventors: E. Premkumar Reddy, Villanova, PA (US); M. V. Ramana Reddy, Upper Darby, PA (US)

(73) Assignee: Temple University - Of the Commonwealth System of Higher Education, Philadelphia, PA (US)

( * ) Notice: Subject to any disclaimer, the term of this patent is extended or adjusted under 35 U.S.C. 154(b) by 133 days.

(21) Appl. No.: 10/018,582

(22) PCT Filed: Jun. 16, 2000

(86) PCT No.: PCT/US00/16725

§ 371 (c)(1),
(2), (4) Date: Dec. 17, 2001

(87) PCT Pub. No.: WO00/77169

PCT Pub. Date: Dec. 21, 2000

Related U.S. Application Data

(60) Provisional application No. 60/139,445, filed on Jun. 16, 1999.

(51) Int. Cl.[7] .................. A61K 31/215; A61K 31/31; A61K 31/275; C07C 67/02; C07C 69/02; C07C 381/00

(52) U.S. Cl. .................. 514/508; 514/522; 514/524; 514/525; 560/231; 560/255; 568/23; 568/24; 568/25

(58) Field of Search ................. 514/508, 522, 514/524, 525; 568/23, 24, 25; 560/231, 255

(56) References Cited

U.S. PATENT DOCUMENTS 6,025,353 A * 2/2000 Masferrer et al.

FOREIGN PATENT DOCUMENTS

| JP | 003037 | * | 1/1997 |
| JP | 9-3037 | | 1/1997 |
| WO | WO 99/18068 | | 4/1999 |

OTHER PUBLICATIONS

Kalgutkar, A. B et al. J. Med. Chem. 1998 41, 4800–4818.*
Chem. Abstr., 162: 185889h., abstracting JP 9–3037.
Kalgutkar et al., J. Med. Chem., 1988 41, 4800–4818.

* cited by examiner

*Primary Examiner*—Paul J. Killos
(74) *Attorney, Agent, or Firm*—Drinker Biddle & Reath LLP

(57) ABSTRACT

Compounds of the formula

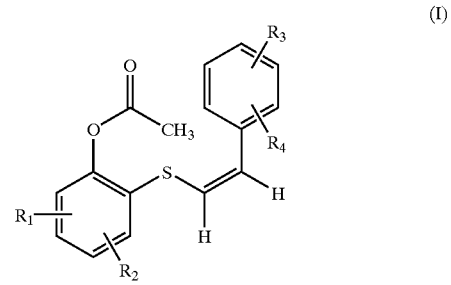

(I)

are provided wherein $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl. The compounds are inhibitors of cyclooxygenase-2 activity, useful for treating inflammation and cyclooxygenase-mediated disorders.

22 Claims, 1 Drawing Sheet

(Z)-STYRYL ACETOXYPHENYL SULFIDES AS CYCLOOXYGENASE INHIBITORS

CROSS-REFERENCE TO RELATED APPLICATION

This is a 371 of PCT/US00/16725, filed Jun. 16, 2000 and published in English on Dec. 21, 2000 as International Publication No. WO 00/77169, which claims the benefit of the filing date of U.S. provisional patent application Ser. No. 60/139,445, filed Jun. 16, 1999, pursuant to 35 U.S.C. 119(e). The entire disclosure of the aforesaid provisional application is incorporated herein by reference.

FIELD OF THE INVENTION

The invention relates generally to anti-inflammatory drugs, and more particularly to novel compounds which inhibit the activity of cyclooxygenase-2.

BACKGROUND OF THE INVENTION

The metabolites of arachidonic acid, such as prostaglandins, lipoxygenases and thromboxane products are produced in a wide variety of tissues and play a key role in several biological responses. Prostaglandins mediate both beneficial and undesirable biological reactions. The production of prostaglandins induces pain, swelling, heat and redness which are characteristic features of inflammation. The chronic inflammation associated with prostaglandin production leads to the breakdown of the injured tissue and angiogenesis. In pathologic chronic inflammation, normal tissues can be destroyed and the new blood vessel formation can support growth of abnormal tissue. Prostaglandins are also important for normal physiological processes in different organs. In the stomach, prostaglandins protect mucosa from acid. They also regulate blood flow and salt-water balance in the kidney. Prostaglandins are also important in platelets aggregation and participate in memory and other cognitive functions.

Prostaglandins are produced from cell membrane phospholipids by a cascade of enzymes. The enzymatic activities involve release of arachidonic acid from the cell membrane by phospholipase $A_2$, followed by the conversion of arachidonic acid to a common prostaglandin precursor, $PGH_2$, by cyclooxygenase (also called prostaglandin H synthase). $PGH_2$ is finally converted to various types of prostaglandins ($PGE_1$, $PGE_2$, $PGI_2$ or prostacyclin, $PGF_{2\alpha}$ and thromboxane) by cell-specific synthases.

Aspirin and other nonsteroidal anti-inflammatory drugs (NSAIDs) block the formation of prostaglandins by inhibiting cyclooxygenase activity. They have analgesic, antipyretic and anti-inflammatory activities. However, chronic treatment with the available NSAIDs often leads to disruption of beneficial prostaglandin-mediated processes. The side effects associated with constant usage of NSAIDs include gastrointestinal (GI) irritation and formation of life-threatening GI ulcers.

A dramatic advance in the field of inflammation research came with discovery of multiple enzymes for each step of the prostaglandin synthase cascade. The research suggested that in some situations, such as inflammation, cyclooxygenase was inducible. The cyclooxygenase known at the time, cyclooxygenase-1 (COX-1), was clearly non-inducible or modulated by glucocorticoids. A second, inducible form of cyclooxygenase known as cyclooxygenase-2 (COX-2) was subsequently identified and cloned by several groups of investigators. COX-1 is the constitutive cyclooxygenase isoform and is mainly responsible for the synthesis of cytoprotective prostaglandins in the GI tract and the synthesis of thromboxane which triggers platelet aggregation in blood platelets. COX-2 is inducible and short lived except in the case of certain tumors where it is constitutively activated. COX-2 expression is stimulated in response to endotoxins, cytokines, hormones, growth factors and mitogens. These observations suggest that COX-1 and COX-2 serve different physiological and pathophysiological functions. Indeed, it has been suggested that COX-1 is responsible for endogenous basal release of prostaglandins and hence is important to the physiological functions of prostaglandins such as GI integrity and renal blood flow. On the other hand, it has been suggested that COX-2 is mainly responsible for the pathological effects of prostaglandins, where induction of the enzyme occurs in response to inflammatory agents, hormones, growth factors and cytokines. See, U.S. Pat. No. 5,604,253, incorporated herein by reference, for a discussion of the advantages of selective COX-2 inhibition. Principally, a selective COX-2 inhibitor is expected to possess similar anti-inflammatory, antipyretic and analgesic properties to a conventional NSAID but with reduced potential for gastrointestinal toxicity, and a reduced potential for renal side effects.

The differential tissue distribution of COX-1 and COX-2 provides an approach to develop selective inhibitors for COX-2 with reduced effect on COX-1, thereby preventing gastric side effects.

A number of selective COX-2 inhibitors have been reported. These include diaryl heterocyclics (Penning et al., *J. Med. Chem*, 40, 1347–1365 (1997); acetoxyphenyl alkyl sulfides (Kalgutkar et al., *J. Med. Chem*, 41,4800–4818 (1998); methane sulfonanilides (Li et al., *J. Med. Chem*, 38, 4897–4905 (1995); and tricyclic inhibitor classes (Wilkerson et al., *J. Med. Chem.*, 38, 3895–3901 (1995). U.S. Pat. No. 5,604,253 discloses N-benzylindol-3-yl propanoic acid derivatives as cyclooxygenase inhibitors.

What is needed are additional COX-2 inhibitors, particularly compounds which selectively inhibit the cyclooxygenase activity of COX-2 over COX-1.

SUMMARY OF THE INVENTION

It is an object of the invention to provide compounds and pharmaceutical compositions thereof for inhibiting the biological activity of COX-2, in particular the cyclooxygenase activity of COX-2.

It is an object of the invention to provide for methods of treating disease conditions which are associated with undesired prostaglandin production and/or secretion.

It is an object of the invention to provide for the treatment of cyclooxygenase-mediated disorders.

It is an object of the invention to provide compounds which selectively inhibit COX-2 over COX-1, and a method for preparing such compounds.

It is a further object of the invention to provide novel polymers prepared by polymerization of the (Z)-styryl acetoxyphenyl sulfides of the invention.

These and other objects of the invention shall become apparent from the following disclosure.

A compound of formula I is provided:

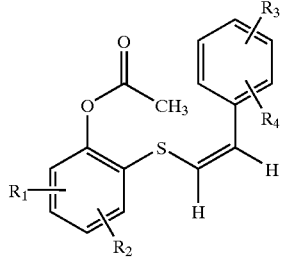

(I)

wherein $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl; or a pharmaceutically acceptable salt thereof. By "sulfamyl" is meant the radical —$SO_2NH_2$. By "lower acylsulfamyl" is meant the radical

wherein $R_5$ is $C_1$–$C_6$ alkyl.

According to one embodiment of the invention, $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, and trifluoromethyl.

According to one preferred embodiment of the invention, $R_1$ and $R_2$ are both hydrogen, and $R_3$ and $R_4$ are independently selected from the group consisting of hydrogen, chloro, fluoro, bromo, hydroxyl, $C_1$–$C_5$ alkyl, $C_1$–$C_3$ alkoxy, nitro, and acetoxy. More preferably, $R_3$ is also hydrogen, and $R_4$ represents 2- or 4-substitution on the phenyl ring to which it is attached. According to another preferred embodiment, $R_1$, $R_2$ and $R_3$ are hydrogen. In such monosubstituted compounds, $R_4$ is most preferably hydrogen or halogen.

According to another embodiment of the invention, a novel intermediate of formula IV is provided, wherein $R_1$, $R_2$, $R_3$ and $R_4$ are defined as above:

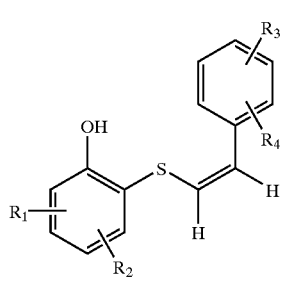

(IV)

According to another embodiment of the invention, a compound according to formula I, or a pharmaceutically acceptable salt thereof, is prepared by reacting a compound of formula IV wherein $R_1$, $R_2$, $R_3$ and $R_4$ are defined as above, with acetic anhydride, and isolating a compound according to formula I from the reaction products.

The formula IV intermediate is preferably provided by reacting a compound of formula II

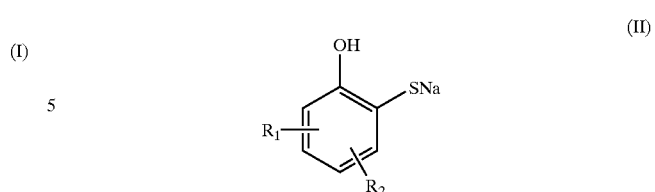

(II)

with a compound of the formula III:

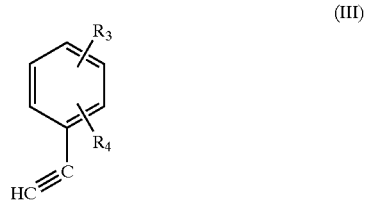

(III)

and isolating a compound according to formula IV from the reaction products.

The invention is also directed to a pharmaceutical composition of one or more compounds of formula I, or a pharmaceutically acceptable salt thereof, in combination with a pharmaceutically effective carrier.

According to yet another embodiment of the invention, a method for treating a cyclooxygenase-mediated disease is provided comprising administering an effective amount of a compound according to formula I, or a pharmaceutically acceptable salt thereof, to an animal in need of such treatment. The expression "animal" is inclusive of human beings.

In yet another embodiment of the present invention, compounds of the formula I may be utilized as monomers in the synthesis of a new class of polymers.

DETAILED DESCRIPTION OF THE INVENTION

Figure 1:
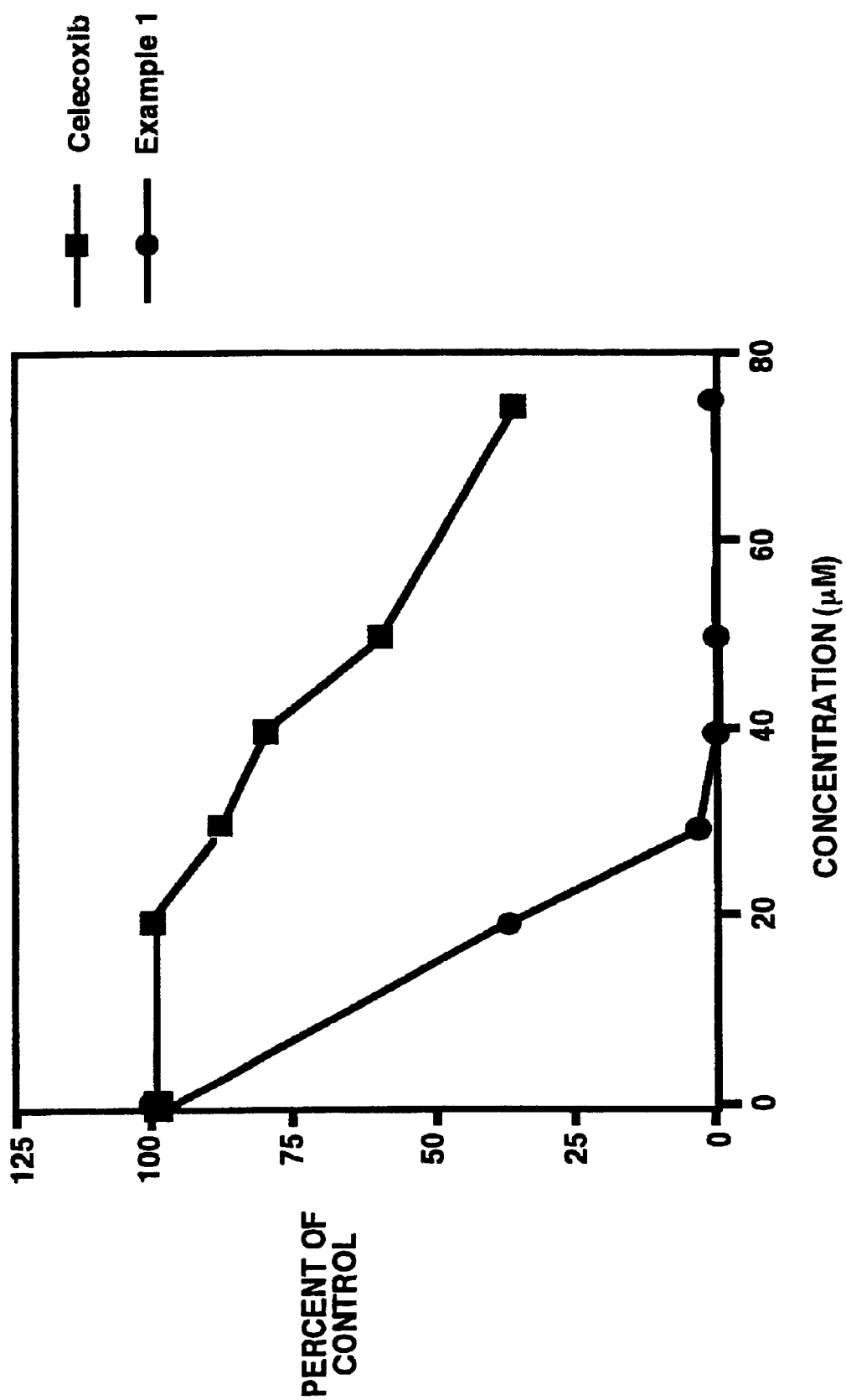
FIG. 1 shows the inhibition of colorectal cancer cell colony growth in the presence of a compound of the invention, as compared to celecoxib.

The compounds of formula I are potent inhibitors of COX-2. COX-2 activity was demonstrated by a cell-free assay in which human recombinant COX-2 was incubated with test compound and [$^{14}$C]-arachidonic acid. The resulting radiolabeled prostanoid compounds, i.e., the products of COX-2 reaction with arachidonic acid, were quantified.

The compounds of the invention are prepared by reaction of a 2-hydroxysodiumphenylthiolate of formula II

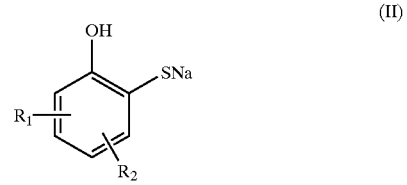

(II)

with an arylacetylene of formula III

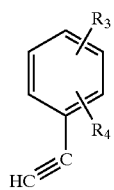

(III)

to yield a (Z)-styryl 2-hydroxyphenylsulfide of formula IV:

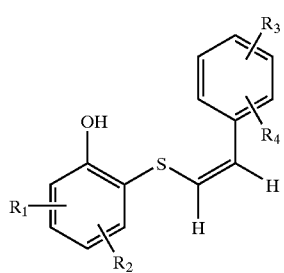

(IV)

The latter is then converted to the corresponding (Z)-styryl 2-acetoxyphenylsulfide of formula I. by reaction with acetic anhydride. The following is the two-part General Procedure for preparation of the formula I compounds.

General Procedure

Synthesis of (Z)-styryl 2-acetoxyphenylsulfides

To a refluxing methanolic solution of a 2-hydroxysodiumphenylthiolate (II) prepared from 460 mg (0.02 g atom) of sodium, 2-hydroxythiophenol (0.02 mol) and 80 ml of absolute methanol, is added a freshly distilled arylacetylene (III). Alternatively, 800 mg (0.02 moles) of NaOH may be used in lieu of the 460 mg of sodium. The mixture is refluxed for 20 hours, cooled and then poured on crushed ice. The crude product is filtered, dried and recrystalized from methanol or aqueous methanol to yield a pure (Z)-styryl 2-hydroxyphenylsulfide (IV).

To a reaction mixture containing the (Z)-styryl 2-hydroxyphenylsulfide (5 mmol), anhydrous pyridine (5 mmol) and acetic anhydride (5 mmol) in dry chloroform (10 ml) is stirred for 5 hours at room temperature (22° C.). The reaction mixture is then diluted with water (20 ml) and shaken well in a separating funnel. The lower organic layer is collected and dried over anhydrous sodium sulfate. Evaporation of the chloroform in vacuum yields the corresponding (Z)-styryl 2-acetoxyphenylsulfide (I) as an oil, or in most cases a colorless solid. The products are purified by TLC or by fractional crystallization.

The compounds of the present invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention preferably are characterized by a selectivity ratio for COX-2 inhibition over COX-1 inhibition of at least about 2, more preferably at least about 10, even more preferably at least about 20, and most preferably at least about 30. COX inhibition may be determined in vitro by enzyme assays well-known to those skilled in the art, such as the enzyme assay method described later herein.

The compounds of the present invention may take the form of pharmaceutically acceptable salts. The term "pharmaceutically acceptable salts", embraces salts commonly used to form alkali metal salts and to form addition salts of free acids or free bases. Where reference is made to "compound of formula I" or a "compound of the invention", it is understood that pharmaceutically acceptable salts are also included. The nature of the salt is not critical, provided that it is pharmaceutically-acceptable. Suitable pharmaceutically acceptable acid addition salts of compounds of formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, .beta.-hydroxybutyric, salicylic, galactaric and galacturonic acid. Suitable pharmaceutically acceptable base addition salts of compounds of formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds of the present invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds of the invention may be administered to individuals (animals, most particularly mammals including humans) afflicted with any disorder characterized by undesirable prostaglandin production resulting from cyclooxygenase activity, particularly COX-2 activity ("cyclooxygenase-mediated disorder"). In particular, the compounds of the invention are believed useful in treating inflamation and inflamation-related disorders, by administering to a subject having or susceptible to such inflamation or inflamation-related disorder and effective amount of a compound according to formula I. Inflamation is associated with a variety of disease conditions. For a list of such disease conditions treatable by cyclooxygenase inhibitors, and COX-2 inhibitors in particular, see U.S. Pat. Nos. 5,604,253 and 5,908,852, the entire disclosures of which are incorporated herein by reference. Such conditions include, for example, arthritis, including but not limited to rheumatoid arthritis, spondyloarthropathies, gouty arthritis, osteoarthritis, systemic lupus erythematosus and juvenile arthritis. Such conditions further include rheumatic fever, symptoms associated with influenza or other viral infections, common cold, low back and neck pain, dysmenorrhea, headache, toothache, sprains and strains, myositis, neuralgia, synovitis, gout and ankylosing spondylitis, bursitis, and following surgical and dental procedures. The compounds of the invention are believed useful as analgesics for treating or alleviating all forms of pain. The compounds are believed useful in the treatment of other disorders including asthma, bronchitis, tendinitis, bursitis; skin related conditions such as psoriasis, eczema, burns and dermatitis; gastrointestinal conditions such as inflammatory bowel disease, Crohn's disease, gastritis, irritable bowel syndrome and ulcerative colitis and for the prevention of colorectal cancer; the treatment of inflamation in such diseases as vascular diseases, migraine headaches, periarteritis nodosa, thyroiditis, aplastic anemia, Hodgkin's disease, sclerodoma, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds of the invention are believed useful as antipyretics for the treatment of fever.

In addition, compounds of formula I may inhibit cellular neoplastic transformations and metastatic tumor growth and hence can be used in the treatment of cancer. In particular, the present invention provides a method for treating or preventing a neoplasia that produces a prostaglandin in a subject in need of such treatment or prevention, the method comprises treating the subject with a therapeutically effective amount of a compound of formula I. The term "neoplasia" includes neoplasia that produce prostaglandins or express a cyclooxygenase, including both benign and cancerous tumors, growths and polyps. Neoplasias believed treatable with cyclooxygenase inhibitors are discussed in U.S. Pat. No. 5,972,986, the entire disclosure of which is incorporated herein by reference. The compounds may be used to inhibit the growth or an established neoplasm, i.e., to induce regression, or to prevent or delay the onset of the neoplasm.

According to U.S. Pat. No. 5,972,986, neoplasias that produce prostaglandins, and which are therefore believed treatable with the compounds of the invention, include brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

The compounds of the invention may also be useful in the treatment of angiogenesis-mediated disorders. Thus, a method for treating, inhibiting or delaying the onset of an angiogenesis-mediated disorder in a subject is provided comprising administering to a subject in need of such treatment an effective amount of a compound according to formula I. Angiogenesis-mediated disorders which may be treatable with cyclooxygenase inhibitors are discussed in U.S. Pat. No. 6,025,353, the entire disclosure of which is incorporated herein by reference. According to U.S. Pat. No. 6,025,353, such disorders include, for example, metastasis, corneal graft rejection, ocular neovascularization, retinal neovascularization, diabetic retinopathy, retrolental fibroplasia, neovascular glaucoma, gastric ulcer, infantile hemaginomas, angiofibroma of the nasopharynx, avascular necrosis of bone, and endometriosis.

The compounds may be administered by any route, including oral and parenteral administration. Parenteral administration includes, for example, intravenous, intramuscular, intraarterial, intraperitoneal, intranasal, rectal, or subcutaneous administration. The active agent is preferably administered with a pharmaceutically acceptable carrier selected on the basis of the selected route of administration and standard pharmaceutical practice.

The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil, saline solution, aqueous dextrose (glucose) and related sugar solutions, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol.

For oral administration, the active agent may be combined with one or more solid inactive ingredients for the preparation of tablets, capsules, or other suitable oral dosage forms. For example, the active agent may be combined with carboxymethylcellulose calcium, magnesium stearate, mannitol and starch, and then formed into tablets by conventional tableting methods.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.01 to about 150 mg/kg/day may be utilized. Higher or lower doses are also contemplated.

The (Z)-styryl acetoxyphenyl sulfides of the present invention may be utilized as monomers in the synthesis of polymers of formula V having pendant aryl and acetoxyphenyl sulfide groups. The polymerization is accomplished by heating the monomer above 250° C. in the presence of a free radical initiator. The initiator may comprise benzoyl peroxide, for example:

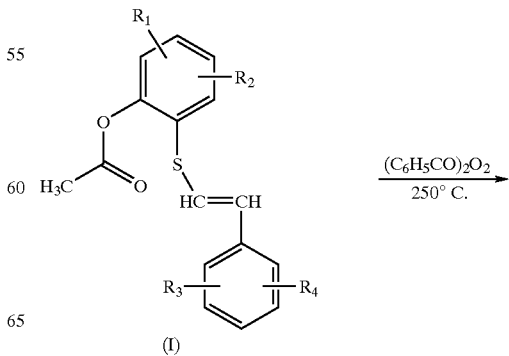

-continued

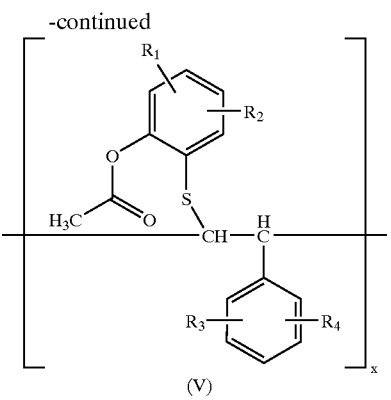

The degree of polymerization "x" in formula V may range from about 10 to about 150, providing an oligomer or polymer of from 5,000 to 50,000 daltons. Other degrees of polymerization are also contemplated.

The practice of the invention is illustrated by the following non-limiting examples.

EXAMPLE 1

Z-styryl 2-acetoxyphenylsulfide

A solution of 2-hydroxythiophenol (10 mmol), phenylacetylene (10 mmol) and sodium (0.01 g atom) was subjected to the General Procedure. The title compound was obtained in 73% yield.

EXAMPLE 2

Z-4-Fluorostyryl 2-acetoxyphenylsulfide

A solution of 2-hydroxythiophenol (10 mmol), 4-fluorophenylacetylene (10 mmol) and sodium (0.01 g atom) was subjected to the General Procedure. The title compound was obtained in 78% yield.

EXAMPLE 3

Z-2-Chlorostyryl 2-acetoxyphenylsulfide

A solution of 2-hydroxythiophenol (10 mmol), 2-chlorophenylacetylene (10 mmol) and sodium (0.01 g atom) was subjected to the General Procedure. The title compound was obtained in 68% yield.

EXAMPLE 4

Z-4-Chlorostyryl 2-acetoxyphenylsulfide

A solution of 2-hydroxythiophenol (10 mmol), 4-chlorophenylacetylene (10 mmol) and sodium (0.01 g atom) was subjected to the General Procedure. The title compound was obtained in 85% yield.

EXAMPLE 5

Z-4-bromostyryl 2-acetoxyphenylsulfide

A solution of 2-hydroxythiophenol (10 mmol), 4-bromophenylacetylene (10 mmol) and sodium (0.01 g atom) was subjected to the General Procedure. The title compound was obtained in 88% yield.

EXAMPLE 6

Z-4-Methylstyryl 2-acetoxyphenylsulfide

A solution of 2-hydroxythiophenol (10 mmol), 4-methylphenylacetylene (10 mmol) and sodium (0.01 g atom) was subjected to the General Procedure. The title compound was obtained in 68% yield.

EXAMPLE 7

Z-4-Ethylstyryl 2-acetoxyphenylsulfide

A solution of 2-hydroxythiophenol (10 mmol), 4-ethylphenylacetylene (10 mmol) and sodium (0.01 g atom) was subjected to the General Procedure. The title compound was obtained in 62% yield.

EXAMPLE 8

Z-4-n-Pentylstyryl 2-acetoxyphenylsulfide

A solution of 2-hydroxythiophenol (10 mmol), 4-n-pentyl-phenylacetylene (10 mmol) and sodium (0.01 g atom) was subjected to the General Procedure. The title compound was obtained in 58% yield.

EXAMPLE 9

Z-3-Hydroxystyryl 2-acetoxyphenylsulfide

A solution of 2-acetoxythiophenol (10 mmol), 3-hydroxy-phenylacetylene (10 mmol) and sodium (0.01 g atom) was subjected to the General Procedure. The title compound was obtained in 78% yield.

EXAMPLE 10

Z-3-Acetoxystyryl 2-acetoxyphenylsulfide

A solution of 2-hydroxythiophenol (10 mmol), 3-hydroxy-phenylacetylene (10 mmol) and sodium (0.02 g atom) was subjected to the General Procedure. The title compound was obtained in 93% yield.

EXAMPLE 11

Z-4-Methoxystyryl 2-acetoxyphenylsulfide

A solution of 2-hydroxythiophenol (10 mmol), 4-methoxy-phenylacetylene (10 mmol) and sodium (0.01 g atom) was subjected to the General Procedure. The title compound was obtained in 59% yield.

EXAMPLE 12

Z-4-Nitrostyryl 2-acetoxyphenylsulfide

A solution of 2-hydroxythiophenol (10 mmol), 4-nitro-phenylacetylene (10 mmol) and sodium (0.01 g atom) was subjected to the General Procedure. The title compound was obtained in 82% yield.

Analytical data for the above compounds is contained in Table 1:

TABLE 1

| Ex. | Calculated | | Found | |
| --- | --- | --- | --- | --- |
|  | % C | % H | % C | % H |
| 1 | 71.08 | 5.22 | 71.42 | 5.14 |
| 2. | 66.65 | 4.54 | 66.28 | 4.62 |

TABLE 1-continued

| | Calculated | | Found | |
|---|---|---|---|---|
| Ex. | % C | % H | % C | % H |
| 3. | 63.05 | 4.30 | 62.95 | 4.36 |
| 4. | 63.05 | 4.30 | 63.44 | 4.22 |
| 5. | 55.03 | 3.75 | 54.65 | 3.69 |
| 6. | 71.80 | 5.67 | 72.44 | 5.78 |
| 7. | 72.45 | 6.08 | 73.04 | 6.12 |
| 8. | N.D.[1] | N.D. | N.D. | N.D. |
| 9. | 67.11 | 4.93 | 67.66 | 5.01 |
| 10. | 58.44 | 4.90 | 58.94 | 4.86 |
| 11. | 65.19 | 5.84 | 64.95 | 5.80 |
| 12. | N.D. | N.D. | N.D. | N.D. |

[1]N.D. = Not done.

Cyclooxygenase Enzyme Assay

Certain of the compounds were tested for inhibitory activity against COX-1 and COX-2, demonstrating the selective action of the compounds for inhibiting COX-2.

Cyclooxygenase activity of ovine COX-1 (Oxford Biomedical Research Inc.) and human recombinant COX-2 Oxford Biomedical Research Inc.) was assayed by a thin layer chromatography (TLC) method as follows. All inhibitors were dissolved in dimethyl sulfoxide to a stock solution of 5 mM. Human recombinant COX-2 (3 units) or ovine COX-1 (15 units) was incubated with inhibitors at several concentrations in a solution containing 100 mM Tris-HCl, pH7.8, 500 uM phenol and hematin for 90 to 120 minutes at room temperature (24° C.). In controls, equal volumes of DMSO without drug were added to the incubation mixture. After incubation for 90–120 minutes, $[1-^{14}C]$arachidonic acid (50 $\mu$M, 51 mCi/mmol) (DuPont NEN) was added and incubated at 37° C. for 2 minutes. The reaction was terminated by extraction with 1 ml of ethyl acetate. The ethyl acetate layer was transferred into a fresh tube and evaporated to dryness in a Speedvac vacuum dryer. The contents of the tubes were reconstituted in 20 ml of ethyl acetate and spotted on a TLC plate (J. T. Baker, Phillipsburg, N.J.) and developed in a mobile phase containing chloroform/methanol (95:5) at 4° C. Radiolabeled prostanoid compounds (the products of COX enzymatic reaction with radiolabeled arachidonic acid substrate) were quantitated with a radioactivity scanner (Fuji, Phosphorimager). The percentage of total products observed at different inhibitor concentrations was divided by the percentage of the products observed for protein samples pre incubated for the same time with DMSO. The results are shown in Table 2. The compounds are significantly more active in inhibiting COX-2 compared to COX-1.

TABLE 2

Inhibition of Cyclooxygenase Activity (I)

| | | | | | IC$_{50}$($\mu$M) | |
|---|---|---|---|---|---|---|
| Ex. | R$_1$ | R$_2$ | R$_3$ | R$_4$ | COX-2 | COX-1 |
| 1 | H | H | H | H | 0.15 | 5.0 |
| 2 | H | H | H | 4-F | 0.35 | 4.5 |
| 3 | H | H | H | 2-Cl | 0.25 | 4.0 |
| 4 | H | H | H | 4-Cl | 0.2 | 4.0 |
| 10 | H | H | H | 3-acetoxy | 0.7 | 2.0 |

Soft Agar Assays

HT29 Cells

Z-styryl 2-acetoxyphenylsulfide (Example 1) was compared to the COX-2 inhibitor celecoxib in inhibiting the growth of HT29 cells in soft agar. HT29 cells are human colorectal carcinoma cells that overexpress COX-2. HT29 cells grow in soft agar and form tumors in nude mice. The soft agar assay was performed as follows. A layer of bottom agar (8% noble agar) was placed onto 60 mm$^2$ tissue culture dishes. The tumor cells were trypsinized from normal growth flasks while in exponential growth. The cells were counted by using a hemacytometer and 1.0×10$^5$ cells were placed into the top agar mixture containing growth medium, 4% noble agar and various concentrations of drugs. The concentration range was normally between 10 $\mu$M to 75 $\mu$M. The cells were not refed during the assay system; therefore, the cells were treated with one dose of the agents. The plates were stained 20 days later with a 0.05% (w/v) nitroblue tetrazolium solution (which stains only viable cells) for 48 hours. Even at the lowest concentration tested (10 $\mu$M) Z-styryl 2-acetoxyphenylsulfide completely inhibited anchorage independent growth of the COX-2 expressing colorectal carcinoma cells. The same concentration of Z-styryl 2-acetoxyphenylsulfide had little affect on the growth of monolayer cells. This would suggest that one mechanism of growth inhibition by the compounds of the invention is the ability to inhibit signaling events necessary for anchorage independent growth, which is a crucial step during the transformation process. A closer examination of the soft agar plates revealed that the celecoxib plates had many viable cells that never formed colonies even at 50 $\mu$M. These results suggest that the inhibition of colony growth by celecoxib was not due to cell death, but more likely due to cytostatic growth inhibition. The Z-styryl 2-acetoxyphenylsulfide plates were devoid of all staining cells at concentrations above 20 $\mu$M, demonstrating that the compound induces death of HT29 cells at concentrations well below celecoxib.

DLD-1 Cells

The same assay was carried out with DLD-1 cells. Like HT29, DLD-1 cells are human colorectal carcinoma cells that overexpress COX-2. They grow in soft agar and form tumors in nude mice. The results are shown in FIG. 1, the y-axis being the percent of cell colonies remaining in comparison to untreated control cells. Even at the highest concentration tested, celecoxib obtained only about partial inhibition, compared to 100% for the compound of the invention.

All references cited herein are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A compound of the formula:

(I)

wherein $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl; or a pharmaceutically acceptable salt thereof.

2. A compound according to claim 1 wherein $R_1$ and $R_2$ are both hydrogen, and $R_3$ and $R_4$ are independently selected from the group consisting of hydrogen, chloro, fluoro, bromo, hydroxyl, $C_1$–$C_5$ alkyl, $C_1$–$C_3$ alkoxy, nitro, and acetoxy; or a pharmaceutically acceptable salt thereof.

3. A compound according to claim 2 wherein $R_3$ is hydrogen; or a pharmaceutically acceptable salt thereof.

4. The compound according to claim 3 wherein $R_4$ is hydrogen; or a pharmaceutically acceptable salt thereof.

5. The compound according to claim 3 wherein $R_4$ is 2-chloro; or a pharmaceutically acceptable salt thereof.

6. The compound according to claim 3 wherein $R_4$ is 4-chloro; or a pharmaceutically acceptable salt thereof.

7. The compound according to claim 3 wherein $R_4$ is 2-fluoro; or a pharmaceutically acceptable salt thereof.

8. The compound according to claim 3 wherein $R_4$ is 4-fluoro; or a pharmaceutically acceptable salt thereof.

9. The compound according to claim 3 wherein $R_4$ is 3-acetoxy; or a pharmaceutically acceptable salt thereof.

10. A pharmaceutical composition comprising a pharmaceutically acceptable carrier and a compound according to claim 1 or a pharmaceutically acceptable salt thereof.

11. A method for treating inflammation comprising administering to a patient in need of such treatment an effective amount of a compound according to claim 1 or a pharmaceutically acceptable salt thereof.

12. A method for treating a cyclooxygenase-mediated disorder comprising administering to a patient in need of such treatment an effective amount of a compound according to claim 1 or a pharmaceutically acceptable salt thereof.

13. A method for treating inflammation or an inflamation-mediated disorder comprising administering to a subject in need of such treatment an effective amount of a compound according to claim 1 or a pharmaceutically acceptable salt thereof.

14. A method for treating a neoplasia comprising administering to a subject in need of such treatment an effective amount of a compound according to claim 1 or a pharmaceutically acceptable salt thereof.

15. A method for treating an angiogenesis-mediated disorder administering to a subject in need of such treatment an effective amount of a compound according to claim 1 or a pharmaceutically acceptable salt thereof.

16. A compound of the formula:

(IV)

wherein $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl.

17. A compound according to claim 16 wherein $R_1$ and $R_2$ are both hydrogen, and $R_3$ and $R_4$ are independently selected from the group consisting of hydrogen, chloro, fluoro, bromo, hydroxyl, $C_1$–$C_5$ alkyl, $C_1$–$C_3$ alkoxy, nitro, and acetoxy.

18. A method for producing a compound of formula I (I)

wherein $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl, comprising reacting a compound according to formula IV

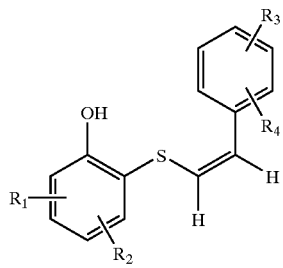

(IV)

wherein $R_1$, $R_2$, $R_3$ and $R_4$ are so defined, with acetic anhydride, and isolating a compound according to formula I.

19. A method according to claim 18 wherein $R_1$ and $R_2$ are both hydrogen, and $R_3$ and $R_4$ are independently selected from the group consisting of hydrogen, chloro, fluoro, bromo, hydroxyl, $C_1$–$C_5$ alkyl, $C_1$–$C_3$ alkoxy, nitro, and acetoxy.

20. A method according to claim 18 wherein the compound of formula IV is provided by reacting a compound of formula II

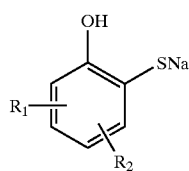

(II)

with a compound of the formula III:

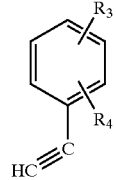

(III)

and isolating a compound according to formula IV from the reaction products, wherein $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl.

21. A compound of the formula:

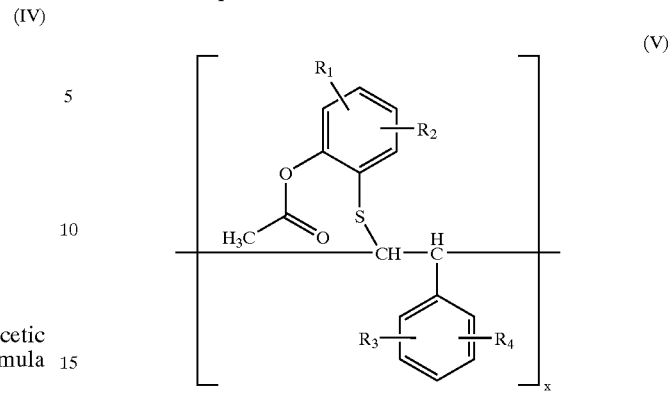

(V)

wherein x is from about 10 to about 150; and $R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy amino, carboxy, sulfamyl, lower acylsulfamyl and trifluoromethyl.

22. A method of preparing a compound according to claim 21 comprising polymerizing a monomer of the formula:

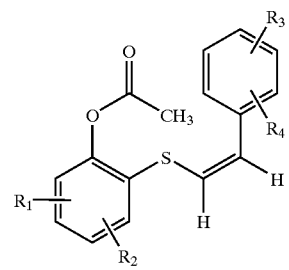

(I)

wherein:

$R_1$, $R_2$, $R_3$ and $R_4$ are independently selected from the group consisting of hydrogen, halogen, hydroxyl, $C_1$–$C_8$ alkyl, $C_1$–$C_6$ alkoxy, nitro, cyano, acetoxy, amino, carboxy, sulfamyl, lower acylsulfamyl and trifluoromethyl.

* * * * *